United States Patent [19]

Arnot et al.

[11] Patent Number: 4,957,869
[45] Date of Patent: Sep. 18, 1990

[54] IMMUNOGENIC PEPTIDE CORRESPONDING TO P. VIVAX CS PROTEIN

[75] Inventors: David E. Arnot; Vincenzo Enea; Ruth S. Nussenzweig; Victor N. Nussenzweig, all of New York, N.Y.

[73] Assignee: New York University, New York, N.Y.

[21] Appl. No.: 180,606

[22] Filed: Apr. 5, 1988

Related U.S. Application Data

[63] Continuation of Ser. No. 754,645, Jul. 12, 1985, abandoned.

[51] Int. Cl.[5] .................. C12N 15/00; C07K 5/00; C07H 15/12
[52] U.S. Cl. .................. 435/320; 435/172.3; 530/328; 536/27; 935/12; 935/29
[58] Field of Search .................. 435/91, 172.3; 536/27; 530/328

[56] References Cited

U.S. PATENT DOCUMENTS

| | | | |
|---|---|---|---|
| 4,466,917 | 8/1984 | Nussenzweig et al. | 260/112 R |
| 4,693,994 | 9/1987 | McCutchan et al. | 514/15 |
| 4,707,357 | 11/1987 | Dame et al. | 424/88 |

OTHER PUBLICATIONS

Dame et al., *Science*, vol. 225:593–599, 1984.
McCutchan et al., *Science*, vol. 225:808–811, 1984.
Rosenberg et al., *Science*, 245:973–976, 1989 (Sep.).
Cochrane et al., *PNAS*, 79:5651 (1982).
Kilejian, *J. Trop. Med. Hyg.*, 29(5) Suppl:1125–1128 (1980).
Nardin et al., *J. Exp. Med.*, 156:20–30 (1982).
Goman et al., *Molecular and Biochem. Parasitology*, 5:391–400 (1982).
Santoro, *J. Bio. Chem.*, 258(5):3341–3345 (1983).
Ellis et al., *Nature*, 302:536–538 (1983).
Lupski et al., *Science*, 220:1285–1288 (1983).
Zavala et al., *J. Exp. Med.*, 157:1947–1957 (1983).
Ozaki et al., *Cell*, 34:815–822 (1983).
Bone et al., *Molecular Biology of Parasites*, Raven Press, NY, pp. 125–134 (1983).
Enea et al., *Science*, 225:628–629 (1984).
Godson et al., *Mole. Parasitology*, 3:127–142 (1984).
Smith et al., *Science*, 224:397–399 (1984).
McCutchan et al., *Science*, 225:625–628 (1984).
Enea et al., *Proc. Natl. Acad. Sci.*, 81:7520–7524 (1984).
Hyde et al., *Mole. and Bio. Parasitology*, 10:269–285 (1984).
Nussenzweig et al., *Phil. Trans. R. Sec. Long.*, B307:117–128 (1984).
Godson et al., *Phil. Trans. R. Soc. Lond.*, B307:129–139 (1984).
Sharma et al., *Science*, 228:879–882 (1985).
Young et al., *Science*, 228:958–962 (1985).
Godson, *Scientific American*, 252:52–59 (1985).
Sharma et al., *Science*, 229:779–782 (1985).

Primary Examiner—Thomas D. Mays
Attorney, Agent, or Firm—Darby & Darby

[57] ABSTRACT

Disclosed are peptides comprising the amino acids

Asp-Arg-Ala-X-Gly-Gln-Pro-Ala-Gly wherein X represents Asp or Ala, said peptides eleciting antibodies against the *P. vivax* circumsporozoite protein. Also disclosed are DNA sequences coding for such peptides.

8 Claims, 6 Drawing Sheets

| | |
|---|---|
| P.vivax | MKNFILAVSSILIVDLFPIHCGNVDLSKAINLNE( )VDASSLGAAHVGQSASRGRGLGENPDDEEGDAKKKKDGKKAEPK |
| P.cynomolgi(G) | —————————F-RG———G VSFNN ———H——EQ-R———————K——GA-KP———E-QV-T- |
| P.vivax | N()PRENKIKQPR()[19 REPEATS OF DRAD/AGQPAG ]    NGAGGQAAGGNAGGGGQGN |
| P.cynomolgi(G) | KS HAK———————E [17 REPEATS, PREDOMINANTLY DGAAAGGGGN ] NARAGDQQPPAGGNKKAGE———————A——— |
| P.vivax | NEGANAPANAKSVKEYLDKLEITVGIEWIPCSVISGVGVRVSRVNAANKKPEDLITLNDLEITDVCTMDKCAGIFNVVSNSLGLVILL |
| P.cynomolgi(G) | ————V————L————IRS-L-V—-S———-C—K——M-SK-S————E-DA————E——— |
| P.vivax | VLALFN |
| P.cynomolgi(G) | ———— |

IMMUNOGENIC PEPTIDE CORRESPONDING TO P. VIVAX CS PROTEIN

The U.S. Government has rights in this invention based upon research support in the form of grant No. AID-DPE-0453-A-00-5012-00 from the Department of State, Agency for International Development.

This is a continuation of application Ser. No. 754,645, filed Jul. 12, 1985, now abandoned.

This application incorporates by reference the entire disclosures of the following copending commonly assigned U.S. patent applications:

(a) Ser. No. 574,124 filed on Jan. 26, 1984 in the name of R. Nussenzweig et al and entitled MALARIA VACCINE—in turn a division of U.S. Ser. No. 234,096 filed on Feb. 21, 1981 now U.S. Pat. No. 4,466,917 issued Aug. 21, 1984;

(b) Ser. No. 574,553 of Ellis, J. et al filed on Jan. 27, 1984 and entitled PROTECTIVE PEPTIDE ANTIGEN;

(c) Ser. No. 633,147 of Ellis, J. et al filed on Jul. 23, 1984 and entitled PROTECTIVE PEPTIDE ANTIGEN CORRESPONDING TO P. falciparum CIRCUMSPOROZOITE PROTEIN;

(d) Ser. No. 649,903 of V. Nussenzweig et al filed on Sept. 12, 1984 and entitled CROSS-REACTIVE AND PROTECTIVE EPITOPES OF CIRCUMSPOROZOITE PROTEINS;

(e) Ser. No. 716,960 of V. Nussenzweig et al filed on Mar. 28, 1985 and entitled SYNTHETIC VACCINE AGAINST P. FALCIPAROM SPOROZOITES.

FIELD OF THE INVENTION

This invention relates to the circumsporozoite (CS) protein of the sporozoite stage of Plasmodium vivax malaria parasite; to a DNA fragment coding for such protein; to immunogenic peptides and proteins comprising an amino acid sequence corresponding to the immunodominant epitope of said CS protein or immunologically active fragments thereof; and to DNA fragments coding for such peptides.

The aforementioned proteins and peptides are useful in inducing an immune response in humans and other animals and in conferring protective immunity in such hosts against infection by P. vivax sporozoites. The DNA fragments are useful in a method for preparing the protein and peptides of the present invention, using known recombinant DNA techniques.

DESCRIPTION OF THE PRIOR ART

It has been shown that immunization of a host with inactivated sporozoites confers protective immunity in such host against infection with sporozoites of the same malarial species: Bruce-Chwatt, L. J. Essential Malariology, William Heineman Ltd. (Publ.) London, 1980. However, immunization with whole inactivated sporozoites is impractical because sporozoites are only available from the glands of infected mosquitoes and are therefore in very short supply.

The immunogenicity of sporozoites of any species resides largely, though not exclusively, in a single antigen, the circumsporozoite (CS) protein. In turn, the immunogenicity of this protein resides in a single epitope which is identically, or quasi-identically repeated many times in tandem.

CS proteins have been identified, analyzed and characterized for some plasmodium species including P. falciparum. Synthetic peptides (produced by chemical synthesis or biological methods) consisting of multiples or analogs of the repeating amino acid sequences have been shown to be immunogenic and are useful in the development of a malaria vaccine.

However, peptides derived from the immunodominant region of the different CS proteins display only species-specific antigenicity.

Therefore, in order to develop a malaria vaccine that would protect humans against infection by any human malaria species, it is necessary to identify, sequence and characterize the CS proteins (or the epitope regions thereof) for all the plasmodium species that infect humans.

Four species of parasitic protozoans cause malaria in humans. Two of these, P. falciparum and P. vivax, predominate. Vivax malaria occurs throughout the world and is the dominant form of malaria in China, Sri Lanka, and Central America. In some areas, such as the Amazon region and Southeast Asia, it is as common as falciparum malaria. Although causing much less mortality than falciparum malaria, vivax malaria with its characteristic relapsing fevers is an incapacitating disease and constitutes a serious public health problem and a barrier to economic development.

Therefore, there is an urgent need to prepare a malaria vaccine for humans, which would be protective against P. vivax infection.

OBJECTS OF THE INVENTION

One object of this invention is to identify and characterize the CS protein of P. vivax malaria parasite and the gene encoding this protein.

Another object of this invention is to identify the amino acid sequence and primary structure of the P. vivax CS protein.

Yet another object of this invention is to provide a peptide or protein sequence associated with the P. vivax CS protein (i.e., comprising a subsequence thereof or an analog or homolog thereof) which is capable of inducing a protective immune response in humans.

Another object of this invention is to provide a peptide or protein comprising an amino acid sequence associated with the immunodominant epitope of the P. vivax CS protein capable of inducing a protective immune response in humans.

Another object of this invention is to provide a DNA sequence coding for immunogenic material capable of inducing a protective immune response in humans against P. vivax malaria infection.

A further object of this invention is to provide the aforementioned peptides and proteins which can be synthesized chemically or by recombinant DNA techniques and other biological methods.

It is also an object of the invention to develop a vaccine that confers protective immunity against infection by P. vivax malaria sporozoites.

These and other objects of this invention will become readily apparent to one of ordinary skill in the art in light of the present description, accompanying claims, and appended drawings.

SUMMARY OF THE INVENTION

One aspect of this invention relates to a peptide comprising the amino acid sequence Asp-Arg-Ala-X-Gly-Gln-Pro-Ala-Gly wherein X represents Asp or Ala, said peptide being capable of eliciting immune response in a host against P. vivax malaria infection.

Another aspect of this invention relates to a DNA fragment coding for the above peptide.

Another aspect of the invention relates to a protein comprising an amino acid sequence consisting essentially of the sequence Asp-Arg-Ala-X-Gly-Gln-Pro-Ala-Gly tandemly repeated at least twice.

Another aspect of this invention relates to a DNA sequence coding for such a protein.

Yet another aspect of the invention relates to a peptide or protein comprising an amino acid sequence corresponding to segments of the amino acid sequence of the CS protein of P. vivax that lie outside the bounds of the tandemly repeated domain of said protein and are substantially homologous to corresponding segments of CS proteins of other species; and to DNA sequences coding for such peptides and proteins.

Still another aspect of this invention relates to the P. vivax CS protein and to DNA coding for this protein.

DETAILED DESCRIPTION OF THE INVENTION

One way to approach the problem of identification of the P. vivax CS protein would have been to make a cDNA clone, from DNA of either the sporozoite or the blood stage of P. vivax parasite. However, use of sporozoite material presents many difficulties as sporozoites are only available in scanty quantities and are contaminated with mosquito thoracic material. In addition, use of cDNA clones is time-consuming and may not reveal the complete structure of the protein of interest.

Although the CS gene does not appear to be well-conserved across species, the following observations have been made:

(a) the presence of immunologically distinct CS epitopes is not a sufficient criterion for assessing overall homology between CS proteins; Enea, E. et al Annali Instituto Superiore to Sanite, Rome (1985); Cochrane, A. H. et al Molec. and Biochem. Parasitol. 14:111 (1985);

(b) at least five immunologically distinct CS proteins of P. cynomolgi strains bear highly homologous sequences outside of the repeating peptide sequence;

(c) the CS genes of P. cynomolgi and P. knowlesi are related; Arnot, D. E., et al., manuscript submitted, 1985; and (d) P. vivax appears to be more closely related to the simian malarias than to the other common human malaria, P. falciparum: Dame, J. B. et al, Science, 225:593 (1984)—these authors are not affiliated with the assignee of this application.

Figure 6:
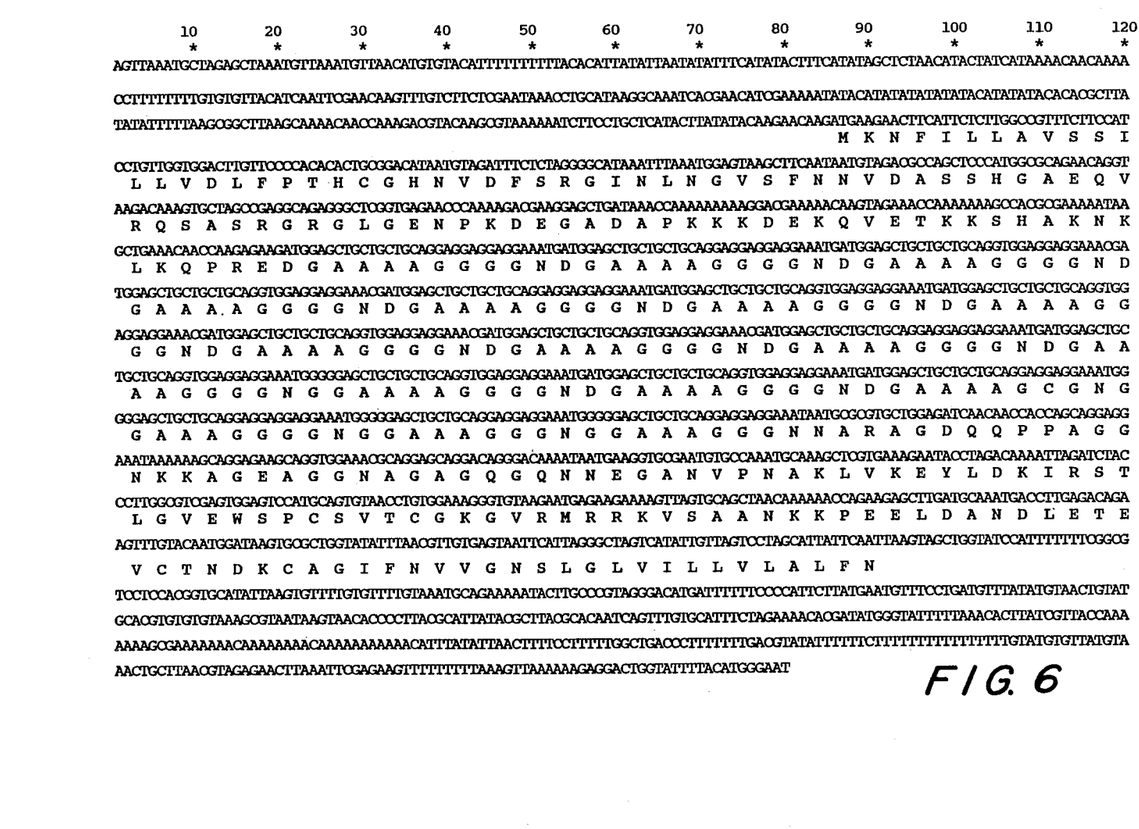
FIG. 6 depicts the complete gene sequence encoding the CS protein of P. cynomolgi.

Therefore, in attempting to identify and sequence the CS protein of P. vivax, the present inventors relied on gene probes of P. cynomolgi. The complete nucleotide sequence of the gene encoding the CS protein of P. cynomolgi has been found by the present inventors and their co-workers and is disclosed in full in FIG. 6, along with its translation.

In search for the sequence of the P. vivax CS protein, DNA isolated from the blood stage of this parasite was size-fractionated, transferred on nitrocellulose, and hybridized with labeled DNA probes from P. cynomolgi CS genes. The probe used was a 700 base-pair Pst I fragment encoding the C-terminal domain and approximately 350 nucleotides of the 3' untranslated region of a cDNA clone of the gene encoding the P. cynomolgi CS protein. Specifically, the probe, designated P236-7, encompasses nucleotides 851 through 1827 (of the sequence shown in FIG. 6) flanked by C and G tails.

Figure 1:
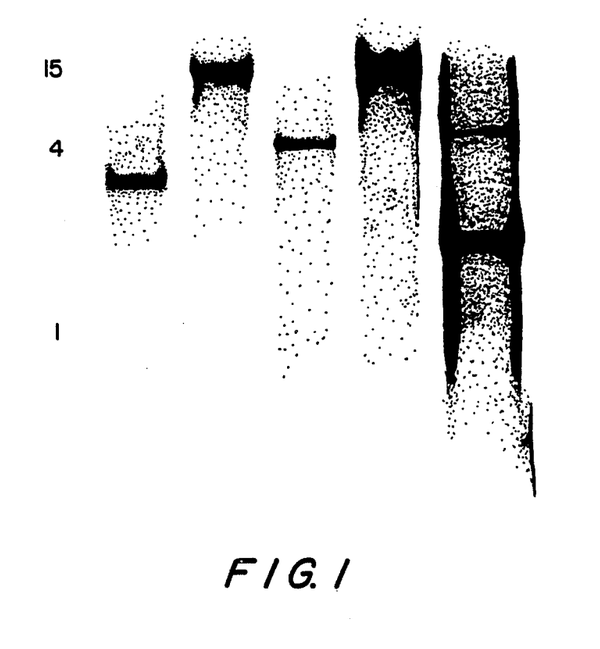
FIG. 1 is an radioautograph of a genomic Southern blot of P. vivax DNA probed with a cDNA clone of P. cynomolgi.

The foregoing P. cynomolgi probe was found to cross-hybridize under medium stringency conditions with single AccI (3.3 kilobases) HpaII(4.2kb) and BglII (15 kb) fragments of P. vivax genomic DNA, as shown in lanes 1-4 of FIG. 1. Lane 5 contains P.cynomolgi (Gombak) genomic DNA cut with BglII.

The procedure used for hybridization was as described in T. Maniatis et al, Molecular Cloning: a Laboratory Manual, Cold Spring Harbor Laboratory (1982), pages 382-389, incorporated by reference herein.

The 15 kb BglII fragment was of a suitable size to be cloned in the bacteriophage lambda EMBL4 vectors according to methods described by Frischauf, A. M. et al, J. Mol. Biol. 170: 827 (1983), the disclosure of which is incorporated by reference in this application. Such vectors (or their DNA) are commercially available from sources such as Promega Biotec, Madison, Wisc., or Vector Cloning Systems, San Diego, Calif.

Isolation of the lambda vector, packaging, handling of the genomic clone, and plaque hybridization, were conducted as described in Maniatis, T., et al, supra, pages 75-85; 256-268; 269-294, and 312-328. The entire disclosure of these sections is incorporated by reference.

Figure 2:
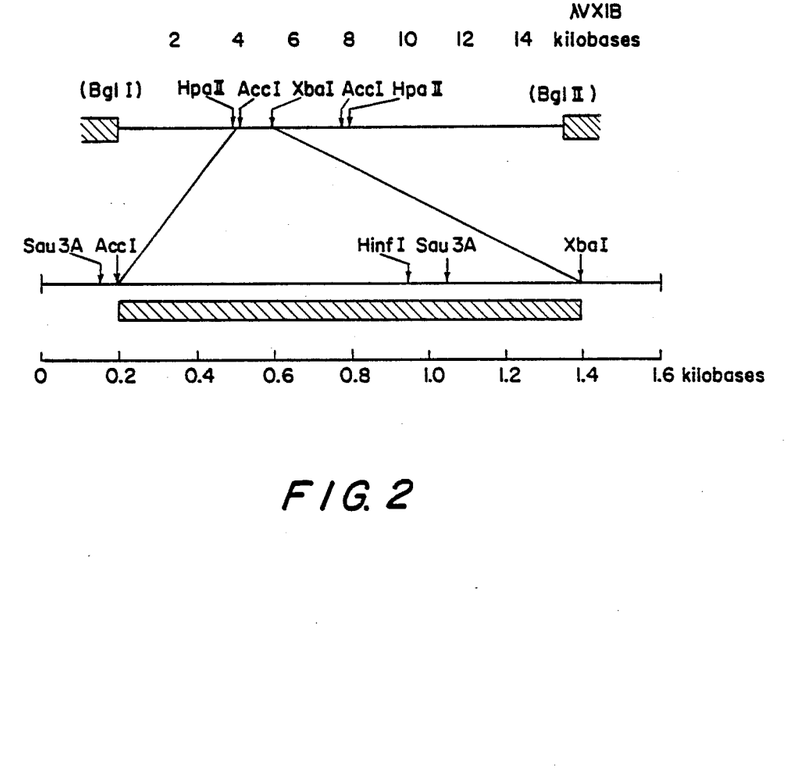
FIG. 2 depicts a coarse and a fine structure map of the lambda phage clone VX1B containing the P. vivax CS gene.

Approximately 5000 plaques of a size-fractionated genomic library of P. vivax were screened using the PstI fragment of the P. cynomolgi (Gombak) cDNA clone as the probe; three positive plaques were obtained The restriction map of one of these clones, indicated as lambda VX1B, is shown in the upper map of FIG. 2. This clone has a map consistent with the sizes of the cross-hybridizing fragments obtained in the genomic Southern blots (FIG. 1, lane 4). A series of plasmid subclones were therefore derived for further mapping and DNA sequence analysis.

A more detailed restriction map of the region cross-hybridizing with the P. cynomolgi cDNA clone is shown in the lower map of FIG. 2. The hatched bar indicates the fragments cross-hybridizing with the cDNA probe.

DNA sequence analysis was initially carried out from the XbaI and the AccI sites, which also occur in the P. cynomolgi CS gene in the same position with respect to the coding sequence of the gene (see FIG. 2).

Sequence homology with the P. cynomolgi gene was detected around these sites and a complete sequence analysis of P. vivax genomic DNA in the region shown in the fine structure map of FIG. 2 was carried out. A continuous open reading frame occurs within this region encoding a protein with a central domain of repeating amino acids flanked by non-repetitive N and C terminal domains substantially homologous to the corresponding domains in the CS genes of P. cynomologi and P. knowlesi. The entire sequence of the P. vivax CS gene and its translation are shown in FIG. 3.

The amino acid sequence encoded by the repeating nucleotide sequence in the thus identified gene is Asp-Arg-Ala-X-Gly-Gln-Pro-Ala-Gly. X stands for either Asp or Ala as illustrated in FIG. 3. This amino acid sequence is repeated 19 times and constitutes 49% of the 373 amino acid protein.

In all the previously identified CS antigens of other plasmodium species, the repetitive amino acid sequence contained the immunodominant epitope of the CS protein. Therefore, it was postulated that the repeated amino acid sequence identified above would in fact compose the immunodominant epitope of the CS protein of P. vivax. This was tested and confirmed by exposing a peptide consisting of a tandem repeat (2x) of the repeating sequence to different concentrations of monoclonal antibody against P. vivax CS protein.

Figure 3:
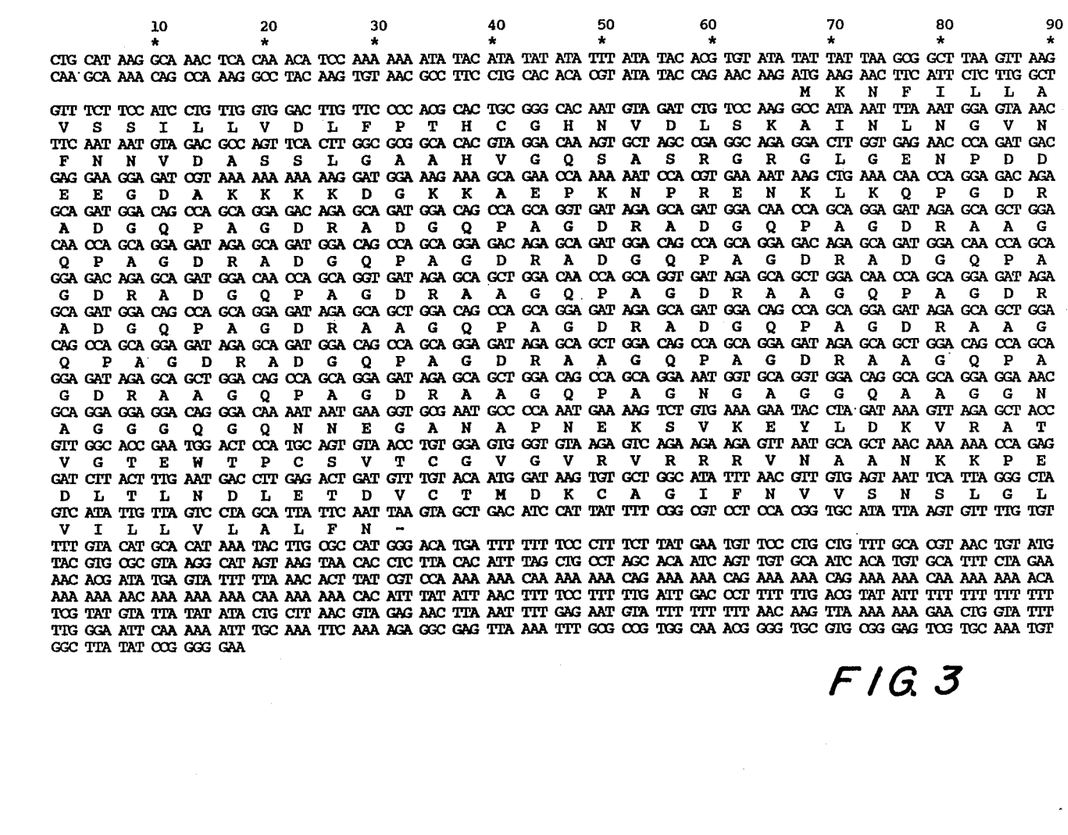
FIG. 3 depicts the complete gene sequence encoding the CS protein of P. vivax, and its translation.

The monoclonal antibody quantitatively bound to a peptide consisting of two tandem repeats of the repeating amino acid sequence of FIG. 3.

More important, this peptide quantitatively inhibited the binding of monoclonal anti-CS to immobilized whole sporozoite extracts.

Based on these observations and on the behavior of peptides corresponding to the repeats of P. knowlesi and P. falciparum CS proteins, peptides containing this repeating sequence (preferably at least twice in tandem) will induce formation of antibodies against P. vivax CS protein, and therefore against P. vivax sporozoites, and will serve to confer protective immunity in humans against infection by this malaria parasite. The complete amino acid sequence of such peptides may also comprise segments other than the repeat unit. The only necessary condition is that the sequence corresponding to the repeating unit(s) of the P. vivax CS protein be available to induce immune response Alternatively, amino acid sequences corresponding to the repeating unit of this CS protein could form part of whole proteins, provided that the immunogenic activity against P. vivax is conserved in such proteins.

As stated above, the immunological test results confirm that the synthetic peptide H(Asp-Gly-Gln-Pro-Ala-Gly-Asp-Arg-Ala)$_2$ contains the immunodominant epitope of the P. vivax CS protein.

Screening of P. vivax sporozoites from strains originating in Thailand, India, El Salvador, Brazil, Sri Lanka, North Korea and Papua New Guinea with the 2F2 antibody indicated that the CS epitope recognized by this antibody is present in all isolates J. Immunol—1985, Zavala, F. et al (in press). These experiments demonstrate that the peptide based on a Brazilian vivax strain protein sequence can compete with the binding of a monoclonal antibody raised against mixed S.E. Asian P. vivax sporozoites to extracts of sporozoites from a New Guinea vivax malaria. Thus, although the P. vivax CS gene was isolated from a Brazilian strain of P. vivax, the epitope deduced from the sequence of the cloned gene appears to be present in all P. vivax CS proteins so far studied. The characterization of this gene and its encoded amino acid sequence allows synthesis of large amounts of the repetitive epitope and other antigenically active regions of the P. vivax CS protein and development of a protective vaccine using peptides corresponding to such regions.

Peptides according to the present invention can be prepared by known chemical synthesis methods, if chain length and properties of the constituent amino acids permit, or by biological methods including recombinant DNA techniques.

Proteins according to the present invention can be prepared by known biological methods including recombinant DNA techniques.

Finally, homologs and analogs of repeating amino acid sequence or multiples thereof may be made in a manner analogous to copending commonly assigned U.S. patent application Ser. No. 695,257 of V. Nussenzweig et al filed on Jan. 28, 1985 and entitled IMMUNODOMINANT EPITOPE OF THE SPOROZOITE SURFACE PROTEIN, incorporated by reference herein.

Figure 4:
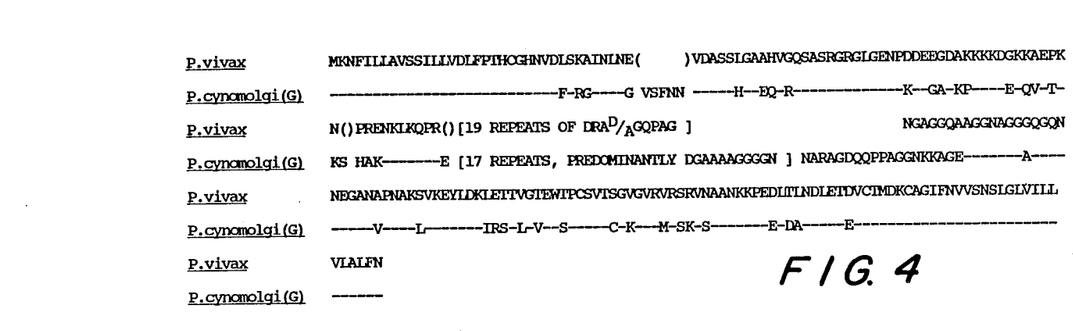
FIG. 4 depicts an alignment of the amino acid sequences encoded by the CS genes of P. vivax and P. cynomolgi and reveals the existence of substantial homology between them.
Figure 5:
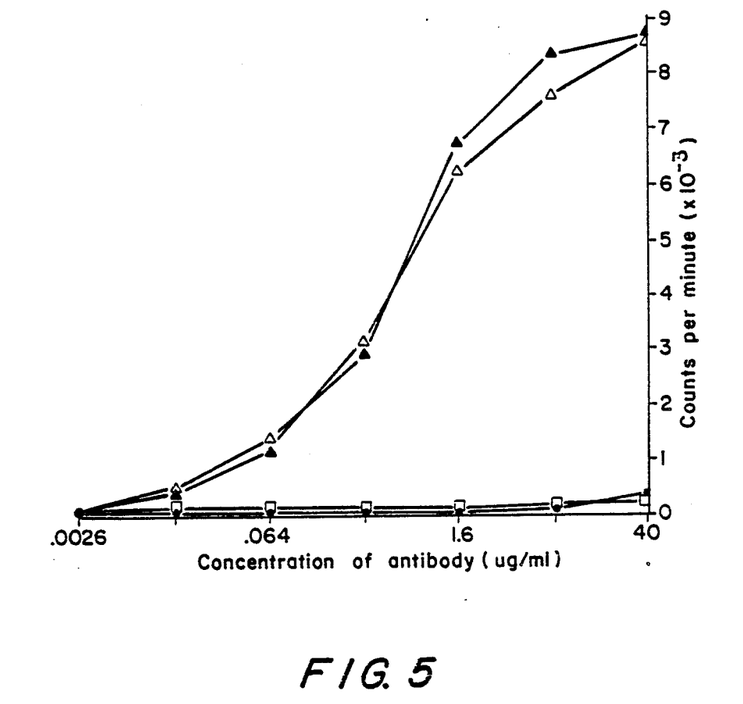
FIG. 5 is a graph depicting: the binding to a peptide according to the present invention of: (a) anti-P. vivax monoclonal antibody—used alone or in the presence of competing concentrations of a peptide according to the present invention, or an unrelated peptide; and (b) an unrelated monoclonal antibody.

In addition to the repeating amino acid sequence of the P. vivax CS protein, two other regions of the P. vivax CS protein are of interest because of their extensive homology to the corresponding regions in the CS protein of P. cynomolgi and P. knowlesi. These homologous sequences are aligned in FIG. 4 and compared with Gombak strain of P. cynomolgi.

Both the N-terminal and the C-terminal domains of the P. vivax and P. cynomolgi protein sequences present substantial homology not only at the nucleotide level, but also at the amino acid level. The two proteins are almost completely identical in thirty amino acids at their N- and C-terminal, which probably constitute conserved hydrophobic leader and transmembrane sequences, respectively.

The *P. knowlesi* sequence is slightly less homologous to the *P. vivax* sequence.

In U.S. patent application Ser. No. 649,903 filed on Sept. 12, 1984 in the name of U. Vergara, et al (the disclosure of which is incorporated by reference herein) the present inventors and their co-workers described a region of *P. falciparum* CS gene neighboring the repeating sequence region that had substantial homology with the corresponding *P. knowlesi* region, were exposed to the parasite surface, and possessed antigenicity. Similarly, the $N_2$ and $C_2$ regions of homology in the *P. vivax* CS protein are expected to be immunogenic and potentially useful in a malaria vaccine preparation because they also are highly conserved between different species.

The $N_2$ region comprises 20 amino acids flanking the repeats in the direction of the N-terminal region. The $C_2$ region lies within two sets of cystein residues which are located close to the C-terminal region.

EXAMPLE 1

DNA Isolation from the Blood Stage of *P. vivax*

Parasitized human red blood cells were purified from white cells by the method of Baggsly and Atkinson, *Trans. Roy. Soc. Trop. Med. Hyg.* 66:4 (1972), incorporated by reference.

Parasite pellets were thawed by stepwise addition of warm (50° C.) 0.1MEDTA (ethylenediaminetetraacetate), pH 8.0, and 0.5% Sarcosyl.

The ratio of buffer per volume of frozen parasite pellet was 10:1. Proteinase K was added to a final concentration of 100 micrograms/ml in the parasite-buffer mixture, which was then incubated at 50° C. for two hours.

Phenol (0.8 volumes, pH 8.2–8.5) was added followed by an equal volume of chloroform. The mixture was stirred and centrifuged at 3000 rpm (about 1,000 g) for five minutes at room temperature.

The lower phase was removed and the phenol/chloroform extraction was repeated as above until the organic phase was clear.

Sodium chloride was added to a final concentration of 0.2 M. Two volumes of ethanol were added and the mixture was incubated at −20° C. for at least two hours.

The mixture was centrifuged at about 3000 g for ten minutes. The pellet was resuspended in a buffer containing 10 mM Tris and 10 mM EDTA, pH 8 (0/10/10 buffer). RNase A was added to a final concentration of 20 micrograms/ml and RNase T1 was added to a final concentration of one unit/ml. The mixture was incubated at 37° C. for 60 minutes.

DNA was precipitated with ethanol and NaCl as above. The precipitated mixture was incubated at −20° C. for 30 minutes, centrifuged at 3,000 g for 10 minutes and the pellet was resuspended in 0/10/10 buffer. Ethanol precipitation was repeated. The precipitate was finally resuspended in 0/10/10 Tris EDTA.

The DNA was passed through a 22 G needle to reduce viscosity (from 5 to 15 times), extracted with phenol/chloroform (as above) two to three times, and precipitated with ethanol as above.

The mixture was centrifuged and the pellet was resuspended in 10 mM Tris, 1 mM EDTA at pH 8.0. The DNA concentration was estimated by running sequential dilutions on a 1% agarose gel along with known amounts of lambda phage DNA.

The DNA was size-fractionated by incubating a BglII digest with Carbowax 8,000 (polyethylene glycol) and NaCl at 7% (weight/volume) and 0.4 M respectively at 37° C. overnight.

EXAMPLE 2

Preparation of Probe and Hybridization

Hybridization of the Southern blot was carried out by in 38% formamide, 6XSSC, 50mM sodium phosphate buffer, pH 6.4, 10% dextran sulphate, 100 micrograms/ml salmon sperm DNA using $3 \times 10^6$ cpm of a probe nick translated using the standard method described in Maniatis, et al, supra.

After overnight hybridization at 42° C., the filters were washed 4 times for 5 minutes at room temperature in 3XSSC, 50 mM sodium phosphate buffer pH6.4, containing 0.1% SDS and then for one minute at 42° C. in the same buffer. Radioautography was carried out at −70° C. with intensifying screens.

EXAMPLE 3

Ligation into Phage and Phage DNA Isolation and Sequencing

The DNA fragment isolated in Example 2 was ligated into EMBL3 as described in Maniatis, T , supra, pages 75–85 and packaged in vitro, using the packaging extract available from Vector Cloning Systems according to the supplier's instructions. A genomic library was constructed as described on pages 269–293 and screened using the same *P. cynomolgi* probe as described on pages 320–322. The hybridization conditions were the same as those of Example 1.

Sequencing took place in accordance with the techniques of Maxam and Gilbert Meth. Enzymol. 65 (Part I): 497–559 (1980); and Sanger Nickler and Coulson, *Proc. Nat'l Acad. Sci.* (U.S.A.) 74:5456 (1977). The gene had an uninterrupted reading frame encoding a protein of 373 amino acids with a molecular weight of 37,253 daltons. The nineteen tandemly repeated units of 9 amino acids each are boxed in FIG. 3. These repeats constitute forty-nine percent (49%) of the total protein. Other general features of CS proteins can be noted, i.e., the central repetitive (immunodominant) epitope, an amino terminal signal sequence, a carboxy terminal hydrophobic transmembrane sequence and several groups of charged residues present in both the N and C terminal regions.

EXAMPLE 4

Peptide Synthesis

An 18-residue peptide amide was synthesized with a structure H-(Asp-Gly-Gln-Pro-Ala-Gly-Asp-Arg-Ala)$_2$. The carboxyl terminus was an alpha carboxamide and not a free carboxylic acid.

The peptide was synthesized using the stepwise solid-phase method of R. B. Merrifield, *J.Am Chem. Soc.* 85: 2149 (1963) on a multidetachable benzhydrylamine resin (p-acyloxy benzhydrylamine—copolystyrene 1% divinyl benzene resin) as described by Tam, J. P. et al *Tetrahedron Lett.*, 2851 (1981). Boc-Ala-p-acyloxybenzhydrylamine resin (0.4 mmol per gram substitution of resin) was placed into the reaction vessel of a Beckman 990M synthesizer and a double coupling protocol via dicyclohexylcarbodiimide was used to give a coupling efficiency more than 99.85% completion per step. The benzyl-based side chain protecting groups and tert-butoxycarbonyl (Boc) for the N-alpha terminus were used. The sequence Asp-Gly is prone to a cyclization reaction to form aspartimide during the synthesis and acid deprotection of the protected peptide-resin. To prevent base catalyzed aspartimide formation during the synthesis and the strong-acid catalyzed deprotection step, a new protection group, Asp (OcHex, aspartyl-Beta cyclohexyl ester) was used as described by Tam, J. P. et al, *Tetrahedron Lett.* 4033, 1979), incorporated herein by reference. The unpurified peptide, when examined by high pressure liquid chromatography gave a single symmetrical peak accounting for more than 83% of all peptide content. The crude peptide was purified by preparative low-pressure liquid chromatography (100–120 psi) on a reversed-phase C-18 column (2.5×30 cm) using aqueous $CF_3CO_2H$ (0.05%) and acetonitrile gradient. The purified material gave a single symmetrical peak on analytical high pressure liquid chromatography and an amino acid analysis gave the correct theoretical values of amino acids. The overall yield based on the first alanine attached to the resin was 72%.

EXAMPLE 5

Recognition of the Peptide of the Present Invention by Monoclonal-Anti CS of *P. Vivax*

Monoclonal-antibody 2F2 from Example 5 was serially diluted in PBS-BSA (indicated in FIG. 5 by black triangles); or in PBS-BSA containing 25 micrograms/ml of synthetic peptide (NANP)$_3$ (indicated by open triangles); or in PBS-BSA containing 25 micrograms/ml of the synthetic peptide of Example 4, i.e. (DRADGQPAG)$_2$ (indicated by black circles).

An unrelated monoclonal-antibody 2A10 (anti-falciparum CS protein) was serially diluted in PBS-BSA (indicated by open squares). 20-5 micrograms/ml of each dilution were delivered to the bottom of microtiter plates which had previously been coated with a synthetic peptide (DRADGQPAG)$_2$ saturated with 1% BSA. After 1 hour of incubation, the wells were washed with PBS-BSA in 50 microliters of $^{125}$I-labelled affinity-purified goat anti-mouse IgG ($10^5$cpm; specific activity about $2\times10^6$cpm/microgram). After an additional hour of incubation, the wells were washed with PBS-BSA and counted. As shown in FIG. 5, 2F2 bound to the immobilized (DRADGQPAG)$_2$ peptide. By contrast, 2A10 did not bind. The binding of 2F2 was totally inhibited by (DRADGQPAG)$_2$, but not affected by (NANP)$_3$.

In other similar experiments, the binding of the anti-*P. falciparum* antibody 2A10 to the corresponding epitope (NANP)$_3$ was not inhibited by the synthetic peptide (DRADGQPAG)$_2$.[1]

1 *A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; Y, tyrosine.*

Similar results are expected to be obtained if (DRAAGQPAG)$_2$ is used instead of (DRADGQPAG)$_2$. In addition, similar results are expected if oligomers of these peptides or of peptides wherein X stands for both alanine and aspartic acid, as the force aminoacid of each repeating unit.

EXAMPLE 6

Inhibition of the Binding of Labelled Monoclonal Antibody 2F2 to Immobilized *P. vivax* extracts by the Synthetic Peptide (Asp-Gly-Gln-Pro-Ala-Gly-Asp-Ala)$_2$ 100,000 cpm of 2F2 antibody labelled by $^{125}$I having a specific activity of about $2\times10^6$ cpm/microgram was diluted in PBS containing 1% BSA. The buffer also contained varying amounts of the synthetic peptide. The mixture was added to microtiter wells coated with *P. vivax* sporozoite extract. After one hour incubation in room temperature, the wells were washed three times with PBS containing 1% BSA and counted in the gamma counter. The results are summarized in Table 1 below.

TABLE I

Inhibition by the synthetic peptide H[Asp—Gly—Gln—Pro—Ala—Gly—Asp—Ala]$_2$ of the binding of $^{125}$I-labeled monoclonal antibody 2F2 to the immobilized *P. vivax* extracts

| Concentration of synthetic peptide (micrograms/ml) | Bound (cpm) |
|---|---|
| 0 | 16,387 ± 1,085* |
| 200 | 842 |
| 20 | 1,091 |
| 2 | 2,130 |
| 0.2 | 3,146 |

*mean ± SD of counts in four wells.

In other preliminary experiments, the binding of the labeled 2F2 monoclonal-antibody to the *P. vivax* extract was shown to be specific since it was inhibited by diluting it in cold 2F2 antibody but not in cold non-relevant monoclonal antibody of the same subclass.

What is claimed is:

1. DNA encoding an immunogenic peptide said peptide comprising the amino acid sequence Asp-Arg-Ala-X-Gly-Gln-Pro-Ala-Gly repeated at least twice wherein X is independently selected from the group consisting of Asp and Ala, said peptide having the property of eliciting formation of antibodies that recognize the immunodominant epitope of the *P. vivax* circumsporozoite surface protein on the surface of sporozoites, said DNA being essentially purified; provided that said peptide is not said surface protein.

2. DNA according to of claim 1 wherein said repeated amino acid sequence is repeated a sufficient number of times to constitute essentially the entire immunodominant epitope region of said *P. vivax* circumsporozoite surface protein.

3. The DNA fragment of claim 1 wherein said repeated amino acid sequence is tandemly repeated up to 19 times.

4. The DNA fragment of claim 1 wherein said repeated amino acid sequence is repeated at least 19 times.

5. DNA according to any one of claims 1 or 2-4 said DNA being incorporated in the DNA of a recombinant microorganism which expresses said peptide.

6. A gene encoding a protein consisting essentially of the circumsporozoite surface protein of *P. vivax* sporozoites, said gene consisting essentially of bases 157 through 1296 of the nucleotide sequence depicted in FIG. 3, said gene being flanked by non Plasmodium nucleic acid sequences, said gene being essentially purified.

7. DNA encoding a polypeptide consisting essentially of the amino acid sequence:

```
M K N F I L L A V S S I L L V D L F P T H C G H N V D L S K A I N
L N E V D A S S L G A A H V G Q S A S R G R G L G E N P D D E E G
D A K K K K D G K K A E P K N P R E N K L K Q P R D R A D G Q P A
G D R A D G Q P A G D R A D G Q P A G D R A A G Q P A G D R A D G
Q P A G D R A D G Q P A G D R A D G Q P A G D R A D G Q P A G D R
A A G Q P A G D R A A G Q P A G D R A D G Q P A G D R A A G Q P A
G D R A D G Q P A G D R A A G Q P A G D R A D G Q P A G D R A A G
Q P A G D R A A G Q P A G D R A A G Q P A G D R A A G Q P A G N G
A G G Q A A G G N A G G G Q G Q N N E G A N A P N A K S V K E Y L
D K L E T T V G T E W T P C S V T C G V G V R V R S R V N A A N K
K P E D L T L N D L E T D V C T M D K C A G I F N V V S N S L G L
V I L L V L A F N
```

8. DNA comprising a nucleotide sequence encoding a peptide comprising the amino acid sequence Gly-Asp-Arg-Ala-Asp-Gly-Gln-Pro-Ala, said peptide having the property of eliciting antibodies that recognize the immunodominant epitope region of *P. vivax* circumsporozoite surface protein, said DNA being essentially purified; provided that said DNA does not consist of the gene encoding the entire *P. vivax* circumsporozoite protein.

* * * * *